United States Patent [19]

Kleinschroth et al.

[11] Patent Number: 4,681,881

[45] Date of Patent: Jul. 21, 1987

[54] 5-ALKOXY-PYRIDO[4,3-d]PYRIMIDINE DERIVATIVES

[75] Inventors: Jüorgen Kleinschroth, Denzlingen; Karl Mannhardt, Elzach-Oberprechtal; Johannes Hartenstein, Stegen-Wittental; Hartmut Osswald, Waldkirch; Bernd Wagner, Denzlingen, all of Fed. Rep. of Germany

[73] Assignee: Godecke Aktiengesellschaft, Berlin, Fed. Rep. of Germany

[21] Appl. No.: 819,961

[22] Filed: Jan. 21, 1986

[30] Foreign Application Priority Data

Jan. 26, 1985 [DE] Fed. Rep. of Germany ....... 3502590

[51] Int. Cl.$^4$ ................... A61K 31/505; C07D 487/04

[52] U.S. Cl. ..................................... 514/258; 544/279
[58] Field of Search ......................... 544/279; 514/258

[56] References Cited

FOREIGN PATENT DOCUMENTS 1050982  3/1986  Japan ................................... 544/279

Primary Examiner—Mark L. Berch
Assistant Examiner—Barbara Cassatt
Attorney, Agent, or Firm—Elizabeth M. Anderson

[57] ABSTRACT

The invention concerns new 5-alkoxy-pyrido[4,3-d]pyrimidine derivatives and pharmacologically acceptable salts thereof, as well as a chemically novel process for their preparation. The new compounds are used in the control of cerebral, cardiac or peripheral vascular diseases or of stenotic symptoms.

5 Claims, No Drawings

5-ALKOXY-PYRIDO(4,3-D)PYRIMIDINE DERIVATIVES

SUMMARY OF THE INVENTION

The invention concerns new 5-alkoxy-pyrido[4,3-d]pyrimidine derivatives of the general Formula Ia

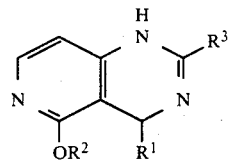
(Ia)

or their tautomeric forms of the general Formulae Ib and Ic

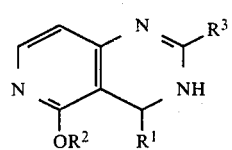
(Ib)

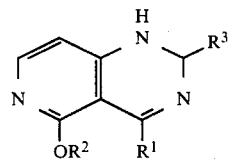
(Ic)

or tautomeric mixtures thereof, wherein $R^1$ represents an unsubstituted or substituted phenyl radical;
$R^2$ is a straight or branched alkyl group with up to six carbon atoms;
$R^3$ is a straight or branched alkyl group with up to six carbon atoms or an unsubstituted or substituted phenyl radical; as well as optionally the pharmacologically acceptable acid addition salts thereof.

The invention also includes a pharmaceutical composition comprising an effective amount of a compound described above together with a pharmacologically acceptable carrier or diluent.

The invention further includes a method of treating vascular diseases comprising administering to a host suffering therefrom an effective amount of a compound described above in unit dosage form.

DETAILED DESCRIPTION

Substituents on the phenyl radical comprise one or more of the same or different groups such as halogen, e.g., fluorine, chlorine, bromine or iodine, nitro, $C_1$–$C_4$ alkyl, e.g., methyl, $C_1$–$C_4$ alkoxy, e.g., methoxy, difluoromethoxy, trifluoromethoxy, dimethylamino or diethylamino, methylthio or trifluoromethyl, or methylenedioxy.

Preferred are 5-alkoxy-pyrido[4,3-d]pyrimidine derivatives of the general Formulae Ia, b, and c, wherein $R^1$ represents phenyl or phenyl substituted in the two and/or three position;
$R^2$ is a $C_1$–$C_4$ alkyl group; and
$R^3$ is a $C_1$–$C_4$ alkyl group or phenyl.

Especially preferred are 5-alkoxy-pyrido[4,3-d]pyrimidine derivatives of the general Formulae Ia, or Ib and Ic, wherein $R^1$ represents phenyl or phenyl substituted by halogen, nitro, methyl, methoxy, difluoromethoxy, trifluoromethoxy, dimethylamino or diethylamino, methylthio or trifluoromethyl, or phenyl disubstituted by methoxy or methylenedioxy radicals or by halogen atoms, which may be the same or different;
$R^2$ is a methyl, ethyl, n-propyl or isopropyl radical; and
$R^3$ is a methyl, ethyl, n-propyl, isopropyl or phenyl radical unsubstituted as in $R^1$ above radical.

The substitution takes place preferably in the two and/or three position and in the two and/or six position.

The compounds of the present invention may be prepared by a process wherein a dihydropyrimidine derivative of the general Formulae IIa

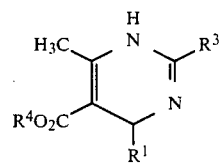
(IIa)

or IIb and IIc

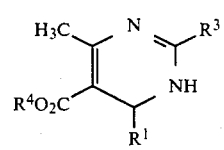
(IIb)

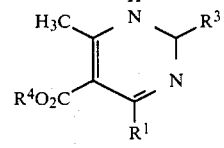
(IIc)

in which $R^1$ and $R^3$ have the above stated meaning and $R^4$ represents a methyl or ethyl group, or tautomeric mixtures thereof, are reacted with s-triazine in the presence of a base and the compounds of the general Formulae IIIa

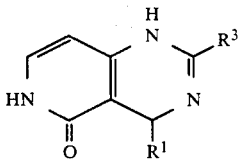
(IIIa)

or IIIb and IIIc

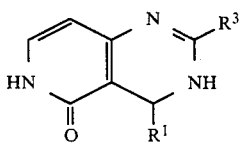
(IIIb)

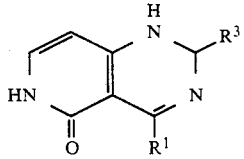
(IIIc)

thus obtained, in which R¹ and R³ have the above stated meaning, or tautomeric mixtures thereof, in a generally known manner are O-alkylated in order to introduce the radical R², and the compounds of the general Formulae Ia, b, and c thus obtained are subsequently converted into their pharmacologically acceptable acid addition salts if desired.

The compounds of the general Formulae IIa, or IIb and IIc, are known from literature (German patent application No. 32 34 684) and can be prepared analogously.

To carry out the chemically novel reaction the dihydropyrimidine derivative is heated to a temperature of 50°–160° C., preferably 100°–150° C., together with s-triazine in an inert organic solvent in the presence of strong bases such as, e.g., alkali alcoholates or sodium hydride. Suitable solvents are mainly polar solvents such as dimethyl sulfoxide, dimethylformamide or ethylene glycol dimethyl ether.

Pursuant to the invention of 5-alkoxy-pyrido[4,3-d]pyrimidine derivatives of the general Formulae Ia, or Ib and Ic, are prepared according to the usual processes for the O-alkylation of lactams as described in the literature (cf. Adv. Heterocyclic Chem. 12 (1970), 185–212). Suitable alkylation agents are alkyl halide and alkyl sulfonates, dialkyl sulfates and trialkyl oxanium salts.

For the reaction with alkyl halides the compounds of the general Formulae IIIa, or IIIb and IIIc, are used in the form of their metal salts, preferably their alkali salts or silver salts, which are either prepared separately or in situ by means of suitable bases such as metal hydrides, carbonates or alkoxides in an aprotic solvent.

Dependent on the alkylation agent used suitable solvents are almost all inert organic solvents such as open-chained, cyclic or aromatic hydrocarbons, e.g., n-pentane n-hexane, cyclohexane, benzene or toluene, halogenated hydrocarbons such as dichloromethane and 1,2-dichloroethane, ethers such as, e.g., diethylether and 1,2-dimethoxyethane, as well as dipolar aprotic solvents such as dimethylformamide, hexamethylphosphoric acid triamide, and dimethyl sulfoxide. Dependent on the solvent used the temperature may vary between −20° C. and the boiling point of the respective solvent.

For reasons of the ambident character of the lactam anion, and dependent on the reaction conditions and alkylation agents use, the alkylation often yields mixtures of O-alkylation and N-alkylation products (J. Org. Chem. 32 (1967), 4040 ff).

The product mixtures thus obtained may be separated by means of the usual chromatographic methods and/or crystallization.

The 5-alkoxy-pyrido[4,3-d]pyrimidine derivatives of the general Formulae Ia, or Ib and Ic, are preferably obtained by reacting the 5-oxo-pyrido[4,3-d]pyrimidines of the general Formulae IIIa, or IIIb and IIIc, with trialkyl oxonium salts, in particular trimethyl oxonium tetrafluoroborate, in an aprotic solvent. The O-isopropyl compounds, on the other hand, are advantageously obtained by alkylation of the alkali metal salts with isopropyl halides.

Dependent on the substituents R¹ and R³ the compounds of the general Formulae Ia, or Ib and Ic, show a more or less basic character at the pyrimidine ring and are therefore, the purification purposes and pharmacotechnological reasons, preferably converted to pharmacologically acceptable crystalline salts. These salts are obtained in the usual manner by neutralizing the bases with the corresponding inorganic or organic acids. As acids may be used, e.g., hydrochloric acid, sulfuric acid, phosphoric acid, hydrobromic acid, acetic acid, tartaric acid, lactic acid, citric acid, malic acid, salicyclic acid, ascorbic acid, malonic acid, or succinic acid.

Since the compounds of the general Formulae Ia, or Ib and Ic, according to the invention show a chiral center either at C-2 or at C-4 they can be present either as racemic mixtures or in the form of the enantiomers. The present invention includes both mixture and enantiomers.

Being calcium antagonists the compounds of the general Formulae Ia, or Ib and Ic, exert vasospasmolytic, vasodilatory, and antihypertensive activities.

For reason of their vasospasmolytic effects the compounds are mainly indicated for the treatment of cerebral, cardiac, and peripheral vascular diseases such as myocardial ischemia, cerebral infarction, pulmonary thromboses, as well as in cases of arteriosclerosis and other stenotic symptoms. The 5-alkoxy-pyrido[4,3-d]pyrimidine derivatives of the present invention are therefore valuable agents for combating cardiovascular mortality. Another subject matter of the present invention is therefore the use of the 5-alkoxy-pyrido[4,3-d]pyrimidines of the general Formulae Ia, or Ib and Ic, in the control of vascular diseases.

The compounds of the general Formulae Ia, or Ib and Ic, according to the invention may be applied in liquid or solid form, orally or parenterally. For the injection-solution mainly water is used containing such additives as stabilizers, solubilizers or buffers as are usual for injection-solutions.

Such additives are, e.g., tartrate and citrate buffers, ethanol, complex formers (such as ethlenediamine tetraacetic acid and the nontoxic salts thereof), as well as high molecular weight polymers (such as liquid polyethylene oxide) to regulate the viscosity. Solid vehicles are, e.g., starch, lactose, mannitol, methylcellulose, talc, highly dispersed silicic acids, higher molecular weight fatty acids (such as stearic acid), gelatine, agar-agar, calcium phosphate, magnesium stearate, animal and vegetable fats, solid high molecular weight polymers (such as polyethylene glycol); if desired preparations suited for oral application may in addition contain flavors and/or sweetening agents.

Enterally administered single doses are in the order of about 5 to 250 mg, preferably 10 to 100 mg. Doses for parenteral application and in the order of about 1 to 20 mg.

Since the compounds of the present invention exist in three possible tautomeric forms or in equilibrium among the three forms, the invention as claimed contemplates the three forms and equilibrium mixtures thereof. For simplicity sake, only one form has been used in the claims.

The following examples serve to illustrate the invention further.

EXAMPLE 1

(±)-1,4-Dihydro-5-isopropoxy-2-methyl-4-phenyl-pyrido[4,3-d]pyrimidine.hydrochloride To a stirred suspension of 1.24 g (41.3 mmol) sodium hydride (80% in oil) in 50 ml dry dimethylformamide are added gradually 8.97 g (37.5 mmol) (±)-1,4,5,6-tetrahydro-2-methyl-5-oxo-phenyl-pyrido[4,3-d]pyrimidine in solid form. When the gas generation diminishes stirring is continued at room temperature for 30 minutes; subsequently 9.56 (56.2 mmol) isopropyl iodide in 20 ml dimethylformamide are added dropwise.

Stirring is continued at room temperature for 72 hours, the solvent distilled under vacuum, and the residue mixed with 100 ml water by stirring. The water is decanted, the residue dissolved in dichloromethane and the solution washed again with water. The dichloromethane solution is dried over sodium sulfate and evaporated under vacuum. The residue is subjected to chromatography on silica gel with ethyl acetate/methanol, $NH_3$ sat. 95:5.

The fraction of the $R_f$ 0.3 is dissolved in ether and converted with the calculated quantity of hydrogen chloride in ethyl acetate into the hydrochloride, the hydrochloride then being recrystallized from isopropanol/diisopropyl ether. The hydrochloride of the (±)-1,4-dihydro-5-isopropoxy-2-methyl-4-phenyl-pyrido[4,3-d]pyrimidine is obtained in the form of colorless crystals with a m.p. of 221° C. (decomp.).

During the above described chromatography (±)-1,4,5,6-tetrahydro-6-isopropyl-2-methyl-4-phenyl-pyrido[4,3-d]pyrimidine ($R_f$ 0.1) is isolated as an additional product.

(±)-1,4,5,6-tetrahydro-2-methyl-5-oxo-4-phenyl-pyrido[4,3-d]pyrimidine used as the starting material is prepared in the following manner.

(±)-1,4,5,6-Tetrahydro-2-methyl-5-oxo-4-phenyl-pyrido[4,3-d]pyrimidine

To a stirred suspension of 4.6 g (0.15 mol) sodium hydride (80% in oil) in 60 ml dry dimethylformamide is added dropwise and in nitrogen atmosphere, a solution of 35.9 g (0.14 mol) (±)-1,4-dihydro-2,6-dimethyl-4-phenyl-pyrimidine-5-carboxylic acid ethyl ester in 100 ml dimethylformamide. When the gas generation diminishes stirring is continued at room temperature for 30 minutes; subsequently 11.3 g (0.14 mol) s-triazine in 60 ml dimethylformamide are added dropwise. The reaction mixture is kept at 110° C. for 16 hours and reduced under vacuum when cool. The dark residue is treated with 900 ml acetone in the supersonic bath and filtered off from the undissolved matter. The acetone solution is evaporated under vacuum and the residue subjected to chromatography on silica gel with dichloromethane/methanol 3:1. The fraction of the $R_f$ 0.2 is isolated and recrystallized from ethyl acetate/methanol.

This process yields (±)-1,4,5,6-tetrahydro-2-methyl-5-oxo-4-phenyl-pyrido-[4,3-d]pyrimidine in the form of beige crystals with a m.p. of 263°–264° C.

The following compounds are prepared analogously:
(±)-4-(3-Chlorophenyl)-1,4-dihydro-5-isopropoxy-2-phenyl-pyrido[4,3-d]pyrimidine (1.a) m.p. 78°–82° C. from methanol.
(±)-1,4-Dihydro-5-isopropoxy-4-(3-nitrophenyl-2-phenylpyrido[4,3-d]pyrimidine (1.b) m.p. 112°–114° C. from diisopropylether/ethylacetate
(±)-1,4-Dihydro-5-isopropoxy-2-methyl-4-(2-trifluoromethylphenyl)-pyrido[4,3-d]pyrimidine.hydrochloride (1.c) m.p. 148°–150° C. from diisopropylether/isopropanol
(±)-1,4-Dihydro-5-isopropoxy-2-(3-nitrophenyl)-4-(2-trifluoromethylphenyl)-pyrido[4,3-d]pyrimidine (1.d)
(±)-1,4-Dihydro-5-isopropoxy-2-methyl-4-(2-nitrophenyl)pyrido[4,3-d]pyrimidine (1.e)
(±)-1,4-Dihydro-5-isopropoxy-2-phenyl-4-(2-trifluoromethylphenyl)pyrido[4,3-d]pyrimidine (1.f)
(±)-1,4-Dihydro-5-isopropoxy-2-(2-trifluoromethylphenyl)-4-(2-trifluoromethylphenyl)pyrido[4,3-d]pyrimidine (1.g)

EXAMPLE 2

(±)-1,4-Dihydro-5-methoxy-4-(3-nitrophenyl)-2-phenyl-pyrido[4,3-d]pyrimidine

A 3.5 g (10 mmol) of (±)-1,4,5,6-tetrahydro-4-(3-nitrophenyl)-5-oxo-2-phenyl-pyrido[4,3-d]pyrimidine and 3.0 g (20 mmol) trimethyl oxonium tetrafluoroborate are stirred in 100 ml 1,2-dichloroethane in nitrogen atmosphere and at room temperature for three days. The product is extracted twice with 50 ml saturated sodium hydrogen carbonate solution, the organic phase is separated, dried over sodium sulfate, and reduced under vacuum.

The residue is subjected to chromatography on silica gel with toluene/ethyl acetate 3:1 and the fraction of the $R_f$ 0.35 recrystallized from n-hexane/-diisopropyl ether. The resulting product has the form of pale beige crystals with a m.p. of 75°–80° C.

We claim:
1. A compound of the formula or its tautomers

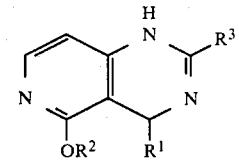

wherein
$R^1$ is phenyl or phenyl substituted by one or two of the same or different substituents selected from halogen, nitro, $C_1$–$C_4$ alkyl, $C_1$–$C_4$ alkoxy, difluoromethoxy, trifluoromethoxy, dimethylamino, diethylamino methylthio, trifluoromethyl, and methylenedioxy;
$R^2$ is a straight or branched alkyl group having one to six carbon atoms;
$R^3$ is a straight or branched alkyl group having up to six carbon atoms, or phenyl or phenyl substituted by one or more of the same or different substituents selected from halogen, nitro, $C_1$–$C_4$ alkyl, $C_1$–$C_4$ alkoxy, difluoromethoxy, trifluoromethoxy, dimethylamino, diethylamino, methylthio, trifluoromethyl, and methylenedioxy, or a pharmocologically acceptable acid addition salt thereof.
2. A compound according to claim 1, wherein
$R^1$ represents phenyl or phenyl mono or disubstituted in the two, three, or six positions;
$R^2$ is a $C_1$–$C_4$ alkyl group; and
$R^3$ is a $C_1$–$C_4$ alkyl group or a phenyl radical.
3. A compound according to claim 2 wherein
$R^1$ represents phenyl or phenyl substituted by halogen, nitro, methyl, methoxy, difluoromethoxy, trifluoromethoxy, dimethylamino, diethylamino, methylthio, or trifluoromethyl, or phenyl disubstituted by methoxy or methylenedioxy or halogen, which may be the same or different;
$R^2$ is methyl, ethyl, n-propyl or isopropyl; and
$R^3$ is methyl, ethyl, n-propyl or phenyl.
4. A pharmaceutical composition comprising a vasospasmolytically effective amount of a compound according to claim 1 together with a pharmacologically acceptable carrier or diluent.
5. A method of treating vascular diseases comprising administering to a host suffering therefrom an effective amount of a composition according to claim 4 in unit dosage form.

* * * * *